United States Patent [19]

Dekeyser et al.

[11] Patent Number: 5,010,068
[45] Date of Patent: Apr. 23, 1991

[54] OXADIAZINYL ORGANOPHOSPHORUS PESTICIDES

[75] Inventors: Mark A. Dekeyser, Waterloo, Canada; Richard C. Moore, Wallingford, Conn.

[73] Assignees: Uniroyal Chemical Company, Inc., Middlebury, Conn.; Uniroyal Chemical Ltd. Ltee., Don Mills, Canada

[21] Appl. No.: 454,668

[22] Filed: Dec. 21, 1989

[51] Int. Cl.$^5$ .................... C07D 273/04; A01N 57/00
[52] U.S. Cl. ......................................... 514/79; 544/68
[58] Field of Search ............................ 544/68; 514/79

[56] References Cited

U.S. PATENT DOCUMENTS 3,238,200  3/1966  Bernstein et al. ...................... 544/68
4,670,555  6/1987  Dekeyser et al. ...................... 544/68

FOREIGN PATENT DOCUMENTS 978854  12/1964  United Kingdom .................. 544/68

OTHER PUBLICATIONS

Chem. Abs. 80:149 33 V (1974).

Primary Examiner—Mary C. Lee
Assistant Examiner—Robert C. Whittenbaugh
Attorney, Agent, or Firm—Glenn E. Karta

[57] ABSTRACT

Organophosphorus-substituted oxadiazines are disclosed which exhibit insecticidal, acaricidal and nematicidal activity, as well as compositions including such compounds, and methods for controlling insects, acarids or nematodes employing such compounds and/or compositions. Also disclosed are novel intermediates useful in the preparation of such compounds.

25 Claims, No Drawings

OXADIAZINYL ORGANOPHOSPHORUS PESTICIDES

BACKGROUND OF THE INVENTION

1. Field of the Invention

This invention is directed to novel organophosphorus-substituted adiazines, which compounds exhibit unexpectedly desirable activity as pesticides, including as soil-applied insecticides, and as acaricides, and nematicides. In other aspects, this invention is directed to pesticidal compositions comprising such compounds as well as to methods of controlling pests employing such compounds and/or compositions. This invention is also directed to novel intermediate compounds useful in the preparation of the present pesticidal compounds.

The destruction by nematodes (especially by so-called root-knot nematodes), acarids and insects presents a serious problem to agriculture. A wide variety of field crops are in need of protection from nematodes, acarids and/or insects including such valuable crops as soybeans, corn, peanuts, cotton, alfalfa and tobacco. In addition, vegetables such as tomatoes, potatoes, sugarbeet, carrots and the like, as well as fruits, nuts, ornamentals and seed bed crops such as apples, peaches, peas, citrus fruit and grapes may also require protection from the ravages of such pests.

Particularly difficult types of insects to control are those which, at one or more stages of their life, inhabit the soil and cause destruction to the roots of agriculturally valuable plants. Representative of this type of insect is the corn rootworm.

Corn rootworms are the larvae of several species of beetles of the genus Diabrotica. Those larvae cause severe damage to the roots of corn plants, particularly in fields where one corn crop follows another in successive seasons. The adult beetles lay their eggs in the soil of a maturing corn crop. The eggs lay dormant in the soil until the following spring. Then they hatch in response to favorable soil temperatures and the larvae feed on the roots of young corn plants causing reduction in yield and/or the stalks to topple over when subjected to either wind or wet soil conditions. The fallen stalks cannot be satisfactorily harvested by mechanical harvesters causing significant losses.

Control of such soil-dwelling insects and nematodes is difficult in that most organophosphorus-type insecticidal and nematicidal compounds have an undesirably short residual life in soil. Accordingly, it is completely unexpected that the novel organophosphorus-substituted oxadiazine compounds of this invention exhibit desirable foliar insecticidal and acaricidal properties coupled with admirable control of soil-dwelling insects and nematodes.

2. Description of related art

British Patent No. 978,854 (1964), relates to thiophosphoric acid esters having contact pesticidal activity against flies, Colorado beetles and red spiders. Those compounds are five membered heterocycles having nitrogen atom of the heterocyclic ring rather than to a carbon atoms, as is the case of the instant invention. Moreover, the present compounds are all six membered heterocycles.

Chemical Abstracts 80:14933v (1974) relates to 1,2,4-oxadiazol-3-yl phosphonothionates and phosphorothionates useful as acaricides, insecticides, nematocides and thickness. However, the thiophosphoric acid ester moiety does not contain any methylene linkage to the oxadiazole structure, unlike the instant invention. Moreover, the compound has a five member heterocycle, in contrast to the six membered heterocycle of the present invention.

U.S. Pat. No. 4,670,555 relates to a class of substituted oxadiazinones having nematocidal and miticidal activity. However, there is no methyl phosphorodithioate moiety attached to the oxadiazinone structure.

Although the above references are directed to compounds used for controlling various pests, there is a continuing need for compounds which exhibit enhanced control of pests, particularly of soil-dwelling insects.

SUMMARY OF THE INVENTION

I one aspect, the present invention is directed to compounds having the formula:

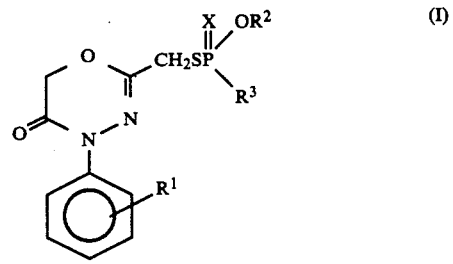

(I)

wherein X is O or S;

$R^1$ is:
hydrogen,
$C_1$–$C_{12}$ alkyl,
$C_2$–$C_{13}$ alkoxy,
$C_7$–$C_9$ aralkyl,
$C_1$–$C_4$ alkylsulfonyl,
nitro,
phenyl or
trihalomethyl, wherein halo is fluorine, chlorine or bromine;

$R^2$ is $C_1$–$C_4$ alkyl; and $R^3$ is $C_1$–$C_4$ alkyl,
$C_1$–$C_4$ alkoxy, or
$C_1$–$C_4$ alkylthio.

The compositions of this invention are comprised of (A) one or more compounds having the structure of formula (I) above, and (B) a suitable carrier. Such suitable carriers may be solid or liquid in nature. The compounds and compositions of the present invention exhibit pesticidal activity, especially against insects, nematodes and acarids.

The present invention also encompasses novel intermediate compounds having the following formula

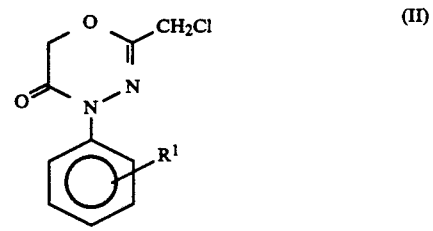

(II)

which are used in the synthesis of the present pesticidal compounds.

DESCRIPTION OF THE PREFERRED EMBODIMENTS

The compounds of this invention may be prepared by reacting a selected substituted 2-(chloromethyl)-4-phenyl-(4H)-1,3,4-oxadiazin-5(6H)-one of formula (II) above with an ammonium thiophosphate or ammonium thiophosphonate of formula (III)

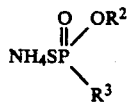

(where $R^1$, $R^2$, $R^3$, and X have the meaning given in formula I) in the presence of 2-propanone. The ammonium thiophosphates are widely used and can be purchased commercially, or be prepared by processes known to the artisan.

Intermediate (II) is prepared by first reacting an appropriately substituted phenylhydrazine with chloroacetic anhydride. This reaction is run in an inert solvent such as diethyl ether, chloroform, toluene $R^1C_6H_4NHNHCOCH_2Cl$, is separated from the reaction mixture and then further reacted with chloroacetyl chloride in 2-butanone to obtain $R^1C_6H_4N(COCH_2Cl)NHCOCH_2Cl$, whihc is then cyclized in the presence of a suitable acid acceptor such as potassium carbonate, pyridine, triethylamine or sodium hydroxide to produce compounds of formula (II).

The compositions of the present invention may be prepared by formulating one or more compounds of the present invention with a suitable carrier, such as a liquid or solid carrier.

Suitable liquid carriers may be comprised of water, alcohols, ketones, phenols, toluene and xylenes. In such formulations, additives conventionally employed in the art may be utilized, such as one or more surface active agents and/or inert diluents, to facilitate handling and application of the resulting pesticide composition.

Alternatively, the pesticidal compounds may be applied in liquid or sprays when utilized in a liquid carrier, such as in a solution comprising a compatible solvent such as acetone, benzene, toluene or kerosene, or as dispersed in a suitable non-solvent medium such as water.

The pesticidal compositions may alternatively comprise solid carriers taking the form of dusts, granules, wettable powders, pastes, aerosols, emulsions, emulsifiable concentrates, and water-soluble solids. For example, the pesticidal compounds of this invention may be applied as dusts when admixed with or absorbed onto powdered solid carriers, such as mineral silicates, e.g., mica, talc, pyrophyllite and clays, together with a surface-active dispersing agent so that a wettable powder is obtained which then is applied directly to the loci to be treated. Alternatively, the powdered solid carrier containing the compounds admixed therewith may be dispersed in water to form a suspension for application in such form.

Granular formulations of the compounds are preferred by broadcasting, side dressing, soil application by broadcasting, side dressing, soil incorporation or seed treatment, and are suitably prepared using a granular or pellitized form of carrier such as granular clays, vermiculite, charcoal or corn cobs. The pesticide is dissolved in a solvent and sprayed onto an inert mineral carrier such as attapulgite granules (10–100 mesh), and the solvent is then evaporated. Such granular compositions may contain from 2–25% pesticide based on carrier plus pesticide, with 3–15% being preferred. In addition, the pesticide may also be incorporated into a polymeric carrier such as polyethylene, polypropylene, butadiene-styrene, styrene-acryonitrile resins, polyamides, poly(-vinyl acetates) and the like. When encapsulated, the pesticide may advantageously be released over an even longer time period, extending its effectiveness further than when used in non-encapsulated form.

Another method of application to loci to be treated is aerosol treatment, for which the compound may be dissolved in an aerosol carrier which is a liquid under pressure but which is a gas at ordinary temperature (e.g., 20° C.) and atmospheric pressure. Aerosol formulations may also be prepared by first dissolving the compound in a less volatile solvent and then admixing the resulting solution with a highly volatile liquid aerosol carrier.

For pesticidal treatment of plants (such term, including plant parts), the compounds of the invention preferably are applied in aqueous emulsions containing a surface-active dispersing agent which may be non-ionic, cationic or anionic. Suitable surface-active agents are well known in the art, and include those disclosed in U.S. Pat. No. 2,547,724 (columns 3 and 4). The compounds of the invention may be mixed with such surface-active dispersing agents, with or without an organic solvent, as concentrates for the subsequent addition of water to yield aqueous suspensions of the compounds at desired concentration levels.

In addition, the compounds may be employed with carriers which themselves are pesticidally active, such as insecticides, acaricides, fungicides or bactericides.

It will be understood that the amount of the pesticidally active compound in a given formulation will depend upon the specific pest to be combatted, as well as upon the specific chemical composition and formulation of the compound being employed, the method of applying the compound/formulation and the locus of treatment so that the pesticidally effective amount of the compound may vary widely. Generally, however, concentrations of the compound as the active ingredient in pesticidally effective formulations may range from about 0.1 to about 95 percent by weight. Spray dilutions may be as low as a few parts per million, while at the opposite extreme, full strength concentrates of the compound may be usefully applied by ultra low volume techniques. When plants constitute the loci of treatment, concentration per unit area may range between about 0.01 and about 50 pounds per acre, with concentrations of between about 0.1 and about 10 pounds Per acre preferably being employed for crops such as corn, tobacco, rice and the like.

When soil is the locus of treatment, the pesticide applied at a rate of from 0.25-12 lbs/a (0.28-13.4 kg/ha). However, it should be considered that in so-called "band" applications, i.e., when the pesticide is placed on or into the soil along with seeds as a band approximately 2-8 inches (5-20 cm) on each side of the row of seeds, the lower end of the range (0.25 lbs./a; 0.28-3.4 kg/ha) may suffice to control corn rootworm. When the pesticide of this invention is spread in a so-called "broadcast" fashion, larger doses may be required, such as 1-12 lbs/a (1.12-13.4 kg/ha).

It is also within the contemplation of this invention that the pesticide be added to the soil in combination with other pesticides, as well as plant nutrients, fertilizers and the like.

To combat pests, sprays of the compounds may be applied to any suitable locus, such as to the pests directly and/or to plants upon which they feed or nest. The pesticidally active formulations may also be applied to the soil or other medium in which the pests are present.

Harmful insects, nematodes and acarids attack a wide variety of plants, including both ornamental and agricultural plants and inflict damage by consuming roots and/or foliage, withdrawing vital juices from the plants, secreting toxins and often by transmitting diseases. The compounds of the present invention may be advantageously utilized to minimize or prevent such damage. The specific methods of application, as well as the selection and concentration of these compounds will of course vary depending upon such circumstances as geographic area, climate, topography, plant tolerance, etc. For specific circumstances, one skilled in the art may readily determine the proper compound, concentration and method of application by routine experimentation.

The compounds of the invention are particularly useful as insecticides, nematocides and acaricides, for foliar and/or soil application. The compounds are particularly effective for controlling insects, such as corn rootworm, which live in the soil during one or more phases of their lives, by means of soil application.

The following examples are given merely to illustrate the scope of the present invention. The invention herein is not intended to be limited to the actual examples provided.

EXAMPLE 1

Preparation of S-(5,6-dihydro-5-oxo-4-phenyl-4H-1,3,-4-oxa-diazin-2-yl)methyl 0,0-diethyl phosphorodithioate (Compound No. 1)

To a stirred solution of 10.0 grams of phenylhydrazine in 200 ml of diethyl ether, cooled to 10° C. in an ice water bath, was added portionwise 13.0 grams of chloroacetic anhydride. After this addition, the mixture was stirred at 10° C. for 1 hour and the resulting precipitate was filtered and washed with diethyl ether. Eight grams of 2-phenylhydrazide of chloroacetic acid were thus obtained.

Four ml of chloroacetyl chloride were added dropwise to a stirred solution of 8 grams of the product of the above reaction in 80 ml of 2-butanone. After this addition, which occurred at room temperature, the mixture was refluxed for four hours, cooled to room temperature and treated with 10 grams of potassium carbonate powder. The mixture was again refluxed for four hours. The mixture was filtered while hot and the solvent then evaporated under reduced pressure, leaving an oil. Seven grams of 2-(chloromethyl)-4-phenyl-4$\underline{H}$-1,3,4-oxadiazin-5(6H)-one intermediate (Compound No. 20) were thus obtained.

Seven grams of ammonium 0,0-diethyl phosphorodithioate were added portionwise to a stirred solution of 7.0 grams of 2-(chloromethyl)-4-phenyl-4H-1,3,4,-oxadiazin-5(6H)-one in 80 ml of 2-propanone. After this addition, which occurred at room temperature, the mixture was stirred for 24 hours, filtered and the oil. Eight grams of S-(5,6-dihydro-5-oxo-4-phenyl-4$\underline{H}$-1,3,4-oxadiazin-2-yl)methyl 0,0-diethyl phosphorodithio (Compound 1) were thus obtained.

The structure was confirmed by nuclear magnetic resonance, as found in Table III.

EXAMPLE 2

Preparation of Compound Nos. 2-28

Additional compounds were prepared applying essentially the synthesis method of Example I. These compounds, including Compound 1, are listed in Tables I and II. Compound Nos. 1-19 are novel pesticides according to the present invention, correspond in structure to Formula (I), and are listed in Table I. Compound Nos. 20-28 are novel intermediates according to the present invention, correspond in structure to Formula (II), and are listed in Table II. Virtually all of the compounds so formed are oils and as such the analytical determinations were substantially confirmed by nuclear magnetic resonance, as found in Table III. In such table, s=singlet; d=doublet; t=triplet; q=quartet; and m=multiplet. The number in parentheses represents the number of Protons. Compound No. 23 was the only solid and had a melting point of 85-87 ° C.

TABLE I

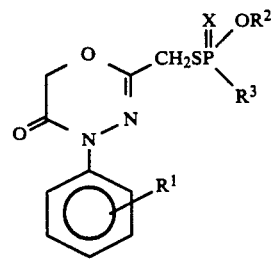

(I)

| Compound No. | R¹ | R² | R³ | X |
|---|---|---|---|---|
| 1 | H | $C_2H_5$ | $OC_2H_5$ | S |
| 2 | 4-$OCH_3$ | $C_2H_5$ | $OC_2H_5$ | S |
| 3 | 4-$CH_3$ | $C_2H_5$ | $OC_2H_5$ | S |
| 4 | 2-$CH_3$ | $C_2H_5$ | $OC_2H_5$ | S |
| 5 | 2-$NO_2$ | $C_2H_5$ | $PC_2H_5$ | S |
| 6 | 2-Cl, 6-$CH_3$ | $C_2H_5$ | $OC_2H_5$ | S |
| 7 | 4-$SO_2CH_3$ | $C_2H_5$ | $OC_2H_5$ | S |
| 8 | 2-$CH_3$ | $C_2H_5$ | $SC_3H_7$ | S |
| 9 | 4-$CH_3$ | $C_2H_5$ | $SC_3H_7$ | S |
| 10 | 4-$CH_3$ | $C_2H_5$ | $OCH_3$ | S |
| 11 | 4-$OCH_3$ | $C_2H_5$ | $OCH_3$ | S |
| 12 | H | $C_2H_5$ | $SC_3H_7$ | S |
| 13 | H | $C_2H_5$ | $SC_4H_9$-s | S |
| 14 | H | $C_2H_5$ | $SC_4H_9$-i | S |
| 15 | 2-$CF_3$ | $C_2H_5$ | $OC_2H_5$ | S |
| 16 | 2-$C_6H_5$ | $C_2H_5$ | $SC_3H_7$ | S |
| 17 | 2-$C_6H_5$ | $C_2H_5$ | $OC_2H_5$ | S |
| 18 | 2-$C_6H_6$ | $C_2H_5$ | $SC_4H_9$-i | S |
| 19 | 2-$CF_3$ | $C_2H_5$ | $SC_3H_7$ | S |

TABLE II

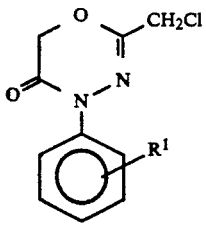

(II)

| Compound No. | R¹ |
| --- | --- |
| 20 | H |
| 21 | 2-Cl, 6-CH₃ |
| 22 | 2-NO₂ |
| 23 | 2-CF₃ |
| 24 | 2-CH₃ |
| 25 | 4-OCH₃ |
| 26 | 4-SO₂CH₃ |
| 27 | 2-CH₃ |
| 28 | 2-C₆H₅ |

TABLE III

Nuclear Magnetic Resonance (NMR) Data (ppm, CDCl₃)

| Compound No. | |
| --- | --- |
| 1 | t(6) 1.3; d(2) 3.7; m(4) 4.2; s(2) 4.7; m(5) 7.2–7.7 |
| 2 | t(6) 1.3; d(2) 3.7; s(3) 3.8; m(4) 4.2; s(2) 4.7; d(2) 6.9; d(2) 7.5 |
| 3 | t(6) 1.3; s(3) 2.3; d(2) 3.7; m(4) 4.2; s(2) 4.75; m(4) 7.1–7.55 |
| 4 | t(6) 1.3; s(3) 2.2; d(2) 3.7; m(4) 4.2; s(2) 4.75; s(4) 7.25 |
| 5 | t(6) 1.4; d(2) 3.75; m(4) 4.2; s(2) 4.8; m(4) 7.4–8.2 |
| 6 | t(6) 1.3; s(3) 2.3; d(2) 3.7; m(4) 4.2; s(2) 4.8; m(3) 7.2–7.4 |
| 7 | t(6) 1.3; s(3) 3.1; m(6) 3.7–4.3; s(2) 4.8; m(4) 7.4–8.0 |
| 8 | t(3) 1.0; t(3) 1.3; m(2) 1.7; s(3) 2.2; m(2) 2.9; d(2) 3.7; m(2) 4.2; s(2) 4.8; s(4) 7.3 |
| 9 | t(3) 1.0; t(3) 1.3; m(2) 1.7; s(3) 2.3; m(2) 2.9; d(2) 3.7; m(2) 4.2; s(2) 4.8; m(4) 7.1–7.5 |
| 10 | s(3) 2.3; d(2) 3.7; d(6) 3.8; s(2) 4.7; m(4) 7.1–7.5 |
| 11 | m(11) 3.5–3.9; s(2) 4.75; d(2) 6.9; d(2) 7.5 |
| 12 | t(3) 1.1; t(3) 1.4; m(2) 1.8; m(2) 3.0; d(2) 3.8; m(2) 4.3; s(2) 4.8; m(5) 7.3–7.7 |
| 13 | t(3) 1.0; m(8) 1.3–2.0; m(1) 3.4; d(2) 3.8; m(2) 4.3; s(2) 4.75; m(5) 7.3–7.7 |
| 14 | d(6) 1.0; t(3) 1.4; m(1) 2.0; m(2) 2.8; d(2) 3.75; s(2) 4.2; s(2) 4.75; m(5) 7.3–7.7 |
| 15 | t(6) 1.4; d(2) 3.7; m(4) 4.2; s(2) 4.8; m(4) 7.5–7.8 |
| 16 | t(3) 1.0; t(3) 1.4; m(2) 1.8; m(2) 2.9; d(2) 3.6; m(2) 4.2; s(2) 4.5; m(9) 7.3–7.5 |
| 17 | t(6) 1.3; d(2) 3.6; m(4) 4.2; s(2) 4.5; m(9) 7.3–7.5 |
| 18 | d(6) 1.0; t(3) 1.4; m(1) 1.9; m(2) 2.85; d(2) 3.6; m(2) 4.2; s(2) 4.5; m(9) 7.3–7.5 |
| 19 | t(3) 1.0; t(3) 1.4; m(2) 1.8; m(2) 2.9; d(2) 3.7; m(2) 4.2; s(2) 4.8; m(4) 7.4–7.8 |
| 20 | s(2) 4.1; s(2) 4.7; m(5) 7.1–7.7 |
| 21 | s(3) 2.3; s(2) 4.1; s(2) 4.8; m(3) 7.2–7.4 |
| 22 | s(2) 4.1; s(2) 4.7; m(4) 7.3–8.2 |
| 23 | s(2) 4.1; s(2) 4.8; m(4) 7.3–7.8 |
| 24 | s(3) 2.2; s(2) 4.1; s(2) 4.8; s(4) 7.3 |
| 25 | s(3) 3.8; s(2) 4.1; s(2) 4.8; m(4) 6.8–7.5 |
| 26 | s(3) 3.1; s(2) 4.2; s(2) 4.9; s(4) 8.0 |
| 27 | s(3) 2.3; s(2) 4.1; s(2) 4.7; m(4) 7.1–7.5 |
| 28 | s(2) 4.0; s(2) 4.5; s(5) 7.3; s(4) 7.4 |

EXAMPLE 3

Preparation of Formulations

The remaining examples relate to the pesticidal use of the compounds of this invention. In all these examples the compounds were diluted to either 500 or 50 parts per million (ppm). To accomplish these dilutions, 0.05 g of the compound in question was dissolved in 10 ml of acetone to which were added 4 drops of a suitable wetting agent. This solution was further diluted with 100 ml of water to provide a 500 ppm suspension. In a similar manner the still more dilute suspension of 50 ppm was prepared.

All the test discussed below, which involved treatment with compounds of this invention at concentrations of 500 and 50 ppm, were always repeated with controls in which the active compound was not provided, to permit a comparison upon which the percent control was calculated.

EXAMPLE 4

Southern Corn Rootworm Test

Test formulations of compounds 1–19 at a concentration of 500 ppm were used. Two ml of the suspension were pipetted onto a filter paper and inserted into a petri dish. Two corn seedlings were also soaked in the chemical preparation and placed in the petri dish. Dishes were held for 18 hours before being loaded with 5 corn rootworm, *Diabrotica undecimounctata*, larvae. After six days, the number of live larvae were noted and the percent control was calculated. The results appear

EXAMPLE 5

Nematode Soil Test

The Southern root-knot nematode, *Meloidogyne incognita*, was reared in sandy culture said using tomato vasahost plant. Roots from culture plants were ground in a blender. Ground roots and culture soil were mixed with equal parts of uninfested soil. This mixture was placed in pots.

Dispersions were prepared using nineteen compounds defined in Table I at a concentration of 1,000 ppm. Each of these dispersions was added to the above-described pots drenching each pot with 25 ml of the dispersion which was further diluted to provide a resultant soil concentration of 50 ppm.

One day after treatment with the 50 ppm dispersions, two tomato seedlings were planted in each Pot. Twelve days after planting, the roots were evaluated by washing away the soil and comparing the number of knots on plant roots from the treated soil with the number of knots noted on untreated nematode-infested controls. These controls were prepared and grown identically with the treated pots. However, these pots were not treated with a dispersion of any of the compounds of this invention. The results of this nematode soil test are summarized below in Table IV.

EXAMPLE 6

Mite Test

Test formulations were prepared having a 500 ppm concentration. Cowpeas, in the first primary leaf stage, were used in the test. Two plants per pot (one primary leaf each) were used for each replicate; two replicates were used for each compound tested. The plants were sprayed with the dispersions using a spray One day following treatment, a circle of tree tanglefoot was placed on the upper surface of the treated leaves and adult mites (*Tetranvchus urticate* Koch) were transferred into this confinement.

Six days following infestation with mites, the plants were examined for adult live mites remaining on the leaves. On an estimated basis in comparison with the number of living mites on the control plants, the percent control was determined.

The results of this mite test are summarized below in Table IV.

TABLE IV

| Compound No. | Corn Rootworm (500 ppm) | Nematode (50 ppm) | Mite (500 ppm) |
|---|---|---|---|
| 1 | 100 | 0 | 0 |
| 2 | 100 | 0 | 0 |
| 3 | 100 | 0 | 0 |
| 4 | 100 | 0 | 96 |
| 5 | 100 | 0 | 0 |
| 6 | 100 | 0 | 0 |
| 7 | 100 | 0 | 0 |
| 8 | 100 | 100 | 100 |
| 9 | 100 | 100 | 100 |
| 10 | 100 | 0 | 0 |
| 11 | 100 | 0 | 0 |
| 12 | 100 | 100 | 91 |
| 13 | 100 | 100 | 95 |
| 14 | 100 | 100 | 96 |
| 15 | 100 | 0 | 0 |
| 16 | 100 | 100 | 95 |
| 17 | 100 | 0 | 0 |
| 18 | 100 | 100 | 98 |
| 19 | 100 | 50 | 95 |

The test results demonstrate surprising and unexpected efficacy of the compounds in controlling corn rootworm in soil application. The compositions also showed good efficacy in control of other insect pests including, but not limited, to mites and root knot nematodes.

It is apparent that various modifications may be made in the formulation and application of the compounds of this invention without departing from the inventive concepts as defined in the following claims.

We claim:

1. A compound having the formula:

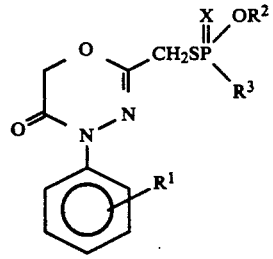

wherein X is O or S;
$R^1$ is:
    hydrogen,
    $C_1$–$C_{12}$ alkyl,
    $C_2$–$C_{13}$ alkoxy,
    $C_7$–$C_9$ aralkyl,
    $C_1$–$C_4$ alkylsulfonyl,
    nitro,
    phenyl or
    trihalomethyl, wherein halo is fluorine, chlorine or bromine;
$R^2$ is $C_1$–$C_4$ alkyl; and
$R^3$ is $C_1$–$C_4$ alkyl
    $C_1$–$C_4$ alkoxy, and
    $C_1$–$C_4$ alkylthio.

2. A compound in accordance with claim 1 wherein $R^1$ is methyl, hydrogen or phenyl; $R^2$ is ethyl; $R^3$ is $C_3$–$C_4$ alkylthio; and X is S.

3. A compound according to claim 2 wherein $R^1$ is methyl and $R^3$ is $C_3$ alkylthio.

4. A compound according to claim 2 wherein $R^1$ is hydrogen and $R^3$ is $C_4$ alkylthio.

5. A compound according to claim 2 wherein $R^1$ is hydrogen and $R^3$ is $C_3$ alkylthio.

6. A compound according to claim 2 wherein $R^1$ is phenyl and $R^3$ is $C_3$ alkylthio.

7. A compound according to claim 2 wherein $R^1$ is phenyl and $R^3$ is $C_4$ alkylthio.

8. An insecticidal, acaricidal or nematicidal composition comprising:
    (A) an effective amount of a compound according to claim 1; and
    (B) a suitable carrier.

9. A composition according to claim 8 wherein $R^1$ is methyl, hydrogen or phenyl; $R^2$ is ethyl; $R^3$ is $C_3$–$C_4$ alkylthio; and X is S.

10. A composition according to claim 9 wherein $R^1$ is methyl and $R^3$ is $C_3$ alkylthio.

11. A composition according to claim 9 wherein $R^1$ is hydrogen and $R^3$ is $C_4$ alkylthio.

12. A composition according to claim 9 wherein $R^1$ is hydrogen and $R^3$ is $C_3$ alkylthio.

13. A composition according to claim 9 wherein $R^1$ is phenyl and $R^3$ is $C_3$ alkylthio.

14. A composition according to claim 9 wherein $R^1$ is phenyl and $R^3$ is $C_4$ alkylthio.

15. An insecticidal, acaricidal or nematicidal method comprising applying a loci to be treated an effective amount of a compound according to claim 1.

16. A method according to claim 15 wherein $R^1$ is methyl, hydrogen or phenyl; $R^2$ is ethyl; $R^3$ is $C_3$–$C_4$ alkylthio; and X is S.

17. A method according to claim 16 wherein $R^1$ is methyl and $R^3$ is $C_3$ alkylthio.

18. A method according to claim 16 wherein $R^1$ is hydrogen and $R^3$ is $C_4$ alkylthio.

19. A method according to claim 16 wherein $R^1$ is hydrogen and $R^3$ is $C_3$ alkylthio.

20. A method according to claim 16 wherein $R^1$ is phenyl and $R^3$ is $C_3$ alkylthio.

21. A method according to claim 16 wherein $R^1$ is phenyl and $R^3$ is $C_4$ alkylthio.

22. A compound having the formula:

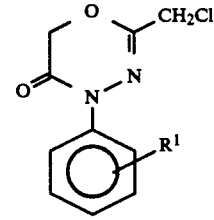

wherein $R^1$ is:
    hydrogen,
    $C_1$–$C_{12}$ alkyl,
    $C_2$–$C_{13}$ alkoxy,
    $C_7$–$C_9$ aralkyl,
    $C_1$–$C_4$ alkylsulfonyl, nitro, phenyl or trihalomethyl, wherein halo is fluorine, chlorine or bromine.

23. A compound according to claim 22 wherein $R^1$ is methyl.

24. A compound according to claim 22 wherein $R^1$ is hydrogen.

25. A compound according to claim 22 wherein $R^1$ is phenyl.

* * * * *